(12) United States Patent
Cheng et al.

(10) Patent No.: US 10,786,404 B2
(45) Date of Patent: Sep. 29, 2020

(54) PACKAGE MADE OF A LAMINATE MATERIAL

(71) Applicant: The Procter & Gamble Company, Cincinnati, OH (US)

(72) Inventors: Enjun Cheng, Beijing (CN); Christian Kohlweyer, Bad Vilbel (DE)

(73) Assignee: The Procter & Gamble Company, Cincinnati, OH (US)

( * ) Notice: Subject to any disclaimer, the term of this patent is extended or adjusted under 35 U.S.C. 154(b) by 172 days.

(21) Appl. No.: 16/140,590

(22) Filed: Sep. 25, 2018

(65) Prior Publication Data
US 2019/0091077 A1    Mar. 28, 2019

(51) Int. Cl.
*A61F 13/551*   (2006.01)
*B31B 70/64*    (2017.01)
(Continued)

(52) U.S. Cl.
CPC .......... *A61F 13/551* (2013.01); *B31B 70/004* (2017.08); *B31B 70/266* (2017.08);
(Continued)

(58) Field of Classification Search
CPC ...... B65D 75/12; B65D 75/26; B65D 75/008; B65D 31/10; B65D 31/02; B65D 85/07;
(Continued)

(56) References Cited

U.S. PATENT DOCUMENTS 3,529,765 A * 9/1970 Wemlinger ............ B65D 31/10
                                                     383/84
3,980,225 A * 9/1976 Kan ...................... B65D 75/008
                                                     383/104
(Continued)

FOREIGN PATENT DOCUMENTS

CN          201111492       9/2008
CN          104071430      10/2014
(Continued)

OTHER PUBLICATIONS

Search Report and Written Opinion for PCT/CN2017/103123 dated May 23, 2018.

*Primary Examiner* — Mollie Impink
(74) *Attorney, Agent, or Firm* — George H. Leal (57) ABSTRACT

A flexible gusset package containing a plurality of items is described. The package has a front surface having no seam; a rear surface opposite the front surface; a first surface adjacent the front and rear surfaces; a second surface having a closing seam and being opposite the first surface; an opposing pair of third and fourth surfaces respectively adjacent the first and second surfaces, the third and fourth surfaces having a first and second side seams, respectively; a pair of side gussets located in the third and fourth surfaces, respectively; and a pair of closing gussets located in the second surface, wherein the surfaces cooperatively define an interior compartment of the package, wherein the package is a laminate having a film layer facing the interior compartment and a paper layer, and wherein the second surface includes an area of the film layer where the closing seam is formed.

17 Claims, 6 Drawing Sheets (51) Int. Cl.
- *B31B 70/26* (2017.01)
- *B31B 70/00* (2017.01)
- *B65D 85/62* (2006.01)
- *B65D 85/07* (2017.01)
- *B65D 65/40* (2006.01)
- *B65D 71/06* (2006.01)
- *B65D 71/36* (2006.01)
- *B31B 160/20* (2017.01)
- *B31B 170/20* (2017.01)
- *B32B 7/12* (2006.01)
- *B32B 27/10* (2006.01)
- *B32B 27/32* (2006.01)
- *B65D 65/10* (2006.01)

(52) U.S. Cl.
CPC .............. *B31B 70/64* (2017.08); *B65D 65/40* (2013.01); *B65D 71/063* (2013.01); *B65D 71/36* (2013.01); *B65D 85/07* (2018.01); *B65D 85/62* (2013.01); *B31B 2160/20* (2017.08); *B31B 2170/20* (2017.08); *B32B 7/12* (2013.01); *B32B 27/10* (2013.01); *B32B 27/32* (2013.01); *B32B 2439/46* (2013.01); *B65D 65/10* (2013.01); *B65D 2571/0066* (2013.01); *B65D 2571/00672* (2013.01); *B65D 2571/00734* (2013.01)

(58) Field of Classification Search
CPC ......... A61F 13/5511; Y10T 428/24769; Y10T 428/24802; Y10T 428/24934; Y10T 428/24793; Y10T 428/31993
USPC .................... 383/116, 125, 102, 121; 428/77
See application file for complete search history.

(56) References Cited

U.S. PATENT DOCUMENTS

| | | | | |
|---|---|---|---|---|
| 2007/0201770 | A1* | 8/2007 | Baner | B65D 33/105 |
| | | | | 383/6 |
| 2009/0084698 | A1* | 4/2009 | Ito | B65D 81/30 |
| | | | | 206/438 |
| 2015/0266663 | A1* | 9/2015 | Joseph | B65D 85/62 |
| | | | | 206/526 |
| 2016/0107826 | A1* | 4/2016 | Motsch | B65D 85/07 |
| | | | | 383/120 |

FOREIGN PATENT DOCUMENTS

| | | |
|---|---|---|
| GB | 191505208 A | 4/1916 |
| JP | 2005-041527 | 2/2005 |
| JP | 2008-018959 | 1/2008 |
| JP | 4364247 | 11/2009 |
| JP | 5420367 | 2/2014 |
| JP | 5600539 | 10/2014 |

* cited by examiner

PACKAGE MADE OF A LAMINATE MATERIAL

FIELD OF THE INVENTION

This invention relates to a substantially parallelepiped-shape package accommodating a plurality of articles which has gussets and seams, a package blank and a wicket bag suitable making the same.

BACKGROUND OF THE INVENTION

Non-fragile, compressible consumer products such as disposable absorbent articles (e.g., diapers and training pants, disposable adult incontinence pants and feminine hygiene pads) are often packaged and sold at retail (i.e., placed on display and for sale in a retail store) in protective packaging, such as boxes, containers, bags, blister packs, cartons, and the like. In addition to being protective, packaging for consumer products is wanted attractive and eye-catching so that consumers might stop and consider purchasing the packaged products.

Flexible packages is widely used for packaging flexible absorbent articles. The flexible package generally comprises a first and second opposite side surfaces. The first side surface may not a seam and the second side surface comprises a pair of gussets each of which is located on the opposite side of the second side surface. The flexible package also includes a front and rear surfaces, and a third and fourth opposite side surfaces having a first and second side seams, respectively. The flexible package also includes a first and second side gussets located in the third and fourth side surfaces.

Such packages may be formed from one or more sheets of polymer film, seamed via application of heating energy, which has caused portions of the film to melt and fuse along the seams.

Package materials, in addition to its basic functions such as protection of articles the package accommodates from external environments, also affect aesthetic impression of the packages. External faces of packages formed by a sheet of polymer film have a glossy appearance which in some areas tends not to be favored by consumers despite many advantageous aspects such as cost and low air and humidity permeability.

Laminates having a film layer and a paper layer conveys warm and nature feelings to consumers especially when the paper layer forms external surfaces of a package. Such laminae having a paper layer may deliver feelings of consumer-favorable nature and hand-craftsmanship. Japanese Unexamined Patent Publication No. 2005-41527 discloses a paper bag made of a craft paper laminated with a synthetic resin film. Japanese Unexamined Patent Publication No. 2008-18959 discloses a package having a cylindrical body which is formed with a space for storing an item and seal parts attached to both end openings of the cylindrical body so as to seal the openings. In the package the cylindrical body is formed of a paper material, and the seal parts are formed of a thermoplastic synthetic resin film.

There is a need for packages that have consumer-desirable perceptual features such as softness, smoothness and other tactile impressions, and creates a visually aesthetic appeal, while being durable enough for shipping and handling.

There is a need for packages that can convey the feeling of nature and hand-craftsmanship.

Further, there is a continuing need for packaging for consumer products that provides a pleasant appearance to eye-catch consumers at the point of sale.

SUMMARY OF THE INVENTION

The present invention provides a flexible gusset package in a substantially parallelepiped-shape containing a plurality of items, the package comprising a front surface; a rear surface opposite the front surface; a first surface adjacent the front and rear surfaces, the first surface having no seam; a second surface opposite the first surface, the second surface having a closing seam; an opposing pair of third and fourth surfaces respectively adjacent the first and second surfaces, the third and fourth surfaces having a first side seam and a second side seam, respectively; a pair of side gussets each of which is located in the third and fourth surfaces, respectively; and a pair of closing gussets located in the second surface, wherein the surfaces cooperatively define an interior compartment of the package, wherein the package comprises a laminate comprising a film layer and a paper layer, the film layer facing the interior compartment, and wherein the second surface comprises an area essentially consisting of the film layer where the closing seam is formed.

The present invention also provides a package blank suitable for forming a package according to the present invention, the blank comprising a first panel forming the front surface and a portion of each of the third and fourth surfaces; a second panel forming the rear surface and a portion of each of the third and fourth surfaces; a third panel located between the first and second panels, the third panel forming the first surface and the pair of the side gussets; a fourth panel adjacent the first panel opposite the third panel, the fourth panel forming a portion of the second surface and a portion of a pair of the closing gussets; and a fifth panel adjacent the second panel opposite the third panel, the fifth panel forming a portion of the second surface and a portion of a pair of the closing gussets. The third panel either comprises recessed lateral edges, or comprises an area adjacent each of its lateral edges which consists of the film layer. Each of the fourth and fifth panels comprises an area essentially consisting of the film layer where the closing seam is formed when the package blank is converted into the package.

The present invention also provides a wicket bag suitable for forming a package according to the present invention, the wicket bag comprising a first panel having a first lateral edge and a second lateral edge; a second panel opposite the first panel, the second panel having a first lateral edge and a second lateral edge, wherein the first and second panel are connected to each other along the first and second lateral edges; a third panel located between the first and second panels, the third panel having a first lateral edge and a second lateral edge; a fourth panel adjacent the first panel opposite the third panel; and a fifth panel adjacent the second panel opposite the third panel; wherein the wicket bag comprises a laminate comprising a film layer and a paper layer, wherein each of the fourth and fifth panels comprises an area essentially consisting of the film layer where a seam is formed when the package blank is converted into the package; wherein the wicket bag comprises a twofold portion formed by a portion of the first panel and a portion of the second panel, and a fourfold portion formed by a portion of the first panel, a portion of the second panel, and the third panel. The third panel either comprises recessed lateral edges or comprises an area adjacent each of its lateral edges which consists of the film layer. Each of the fourth and fifth panels comprises an area essentially consisting of the film layer where a closing seam is formed when the wicket bag is converted into the package.

These and other features, aspects, and advantages of the present invention will become evident to those skilled in the art from a reading of the present disclosure.

DETAILED DESCRIPTION OF THE INVENTION

All ranges are inclusive and combinable. The number of significant digits conveys neither limitations on the indicated amounts nor on the accuracy of the measurements. All numerical amounts are understood to be modified by the word "about" unless otherwise specifically indicated.

The term "absorbent article" as used herein refers to devices which absorb and contain body exudates, and, more specifically, refers to devices which are placed against or in proximity to the body of the wearer to absorb and contain the various exudates discharged from the body. Typical absorbent articles of the present invention include but are not limited to diapers, adult incontinence briefs, training pants, diaper holders and liners, absorbent inserts and the like, as well as feminine hygiene products, such as sanitary napkins and panty liners, and the like. Absorbent articles also include wipes, such as household cleaning wipes, baby wipes, and the like.

"Comprise", "comprises", and "comprising" as used herein are open ended terms, each specifying the presence of what follows, e.g., a component, but not precluding the presence of other features, e.g., elements, steps or components known in the art, or disclosed herein.

"Consist(s) of" and "consisting of" as used herein are close ended terms, each specifying the presence of what follows, e.g., a component, and precluding the presence of other features, e.g., elements, steps or components known in the art, or disclosed herein. "Consist(s) of", and "essentially consist(s) of", "consisting of", and "essentially consisting of", when used directly relative to a laminate having a film layer and a paper layer, means that the laminae does not include the paper layer and only include the film layer.

As used herein the expressions "front", "rear", "outer", "inner", "longitudinal", "transversal", "top", "side", "bottom" and the like, when used to describe the flexible package, relate to a filled package placed in a carrying position with the bottom part facing downwards and the top part facing upwards, such as e.g. shown in the figures. Some of these terms are also used with respect to the methods of manufacturing of the flexible package.

"Lateral edge", when used to describe a package blank or a wicket bag, means an edge parallel to a length direction of the blank or the wicket bag.

"Film" means a sheet structure having a length, width and thickness (caliper), wherein each of the length and width greatly exceed the thickness, i.e., by a factor of 1,000 or more, the structure having one layer (monolayer) or more respectively adjacent layers (multilayer), each layer being a substantially continuous structure formed of one or more thermoplastic polymer resins (including blends thereof).

Package

The present invention provides a flexible gusset package in a substantially parallelepiped-shape containing a plurality of items wherein the package comprises a laminate comprising a film layer and a paper layer, the film layer facing the interior compartment. The package according to the present invention may provide consumer-desirable features such as softness, smoothness and other tactile impressions, and creates a visually aesthetic appeal, while being durable enough for shipping and handling. The package may conveys the feeling of nature and hand-craftsmanship using paper or paper-like looking material for the paper layer.

Figure 1A:
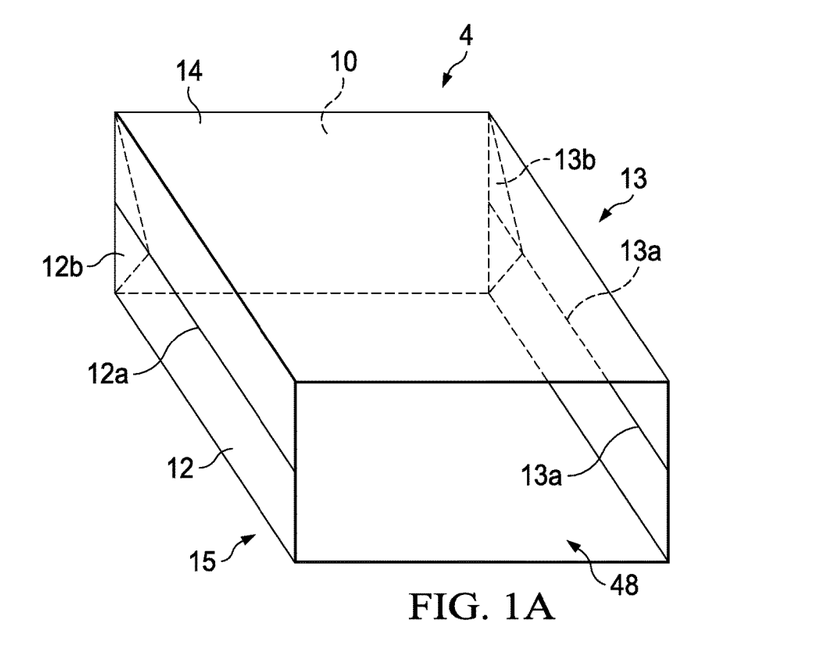
FIG. 1A is a perspective view of a flexible open bag structure from which a package according to the present invention may be formed.
Figure 1B:
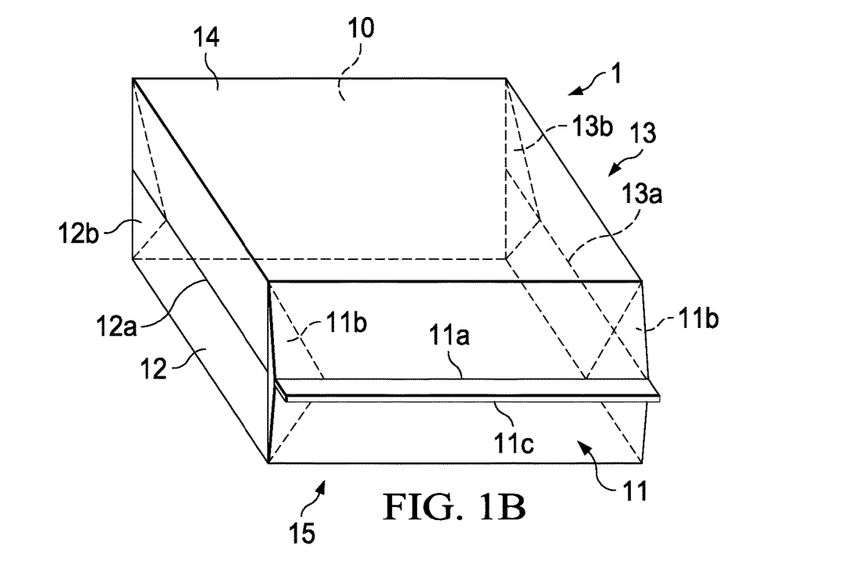
FIG. 1B is a perspective view of an exemplary package according to the present invention.
Figure 1C:
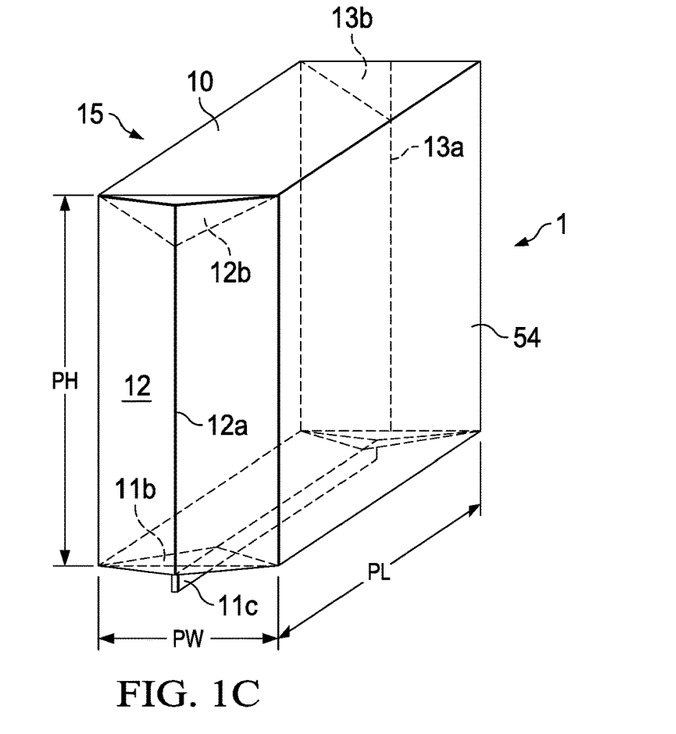
FIG. 1C is an alternative perspective view of the package shown in FIG. 1B.

Referring to FIGS. 1A-1C, an exemplary package 1 according to the present invention and a flexible open bag 4 suitable for manufacturing the package 1 comprise a laminate comprising a film layer and a paper layer which is flexible such that the package 1 may assume the parallelepiped-shape when it is filled with articles.

The manufacture of the package 1 may start from a single sheet of a partial laminate stock comprising a paper layer, a film layer, and an area which does not have the paper layer. The laminate is suitably folded to form bag gussets 12b, 13b and then joined along portions by bonding to form two side seams 12a, 13a on opposite sides, to form the bag structure 4 having a first surface 10, a third and a fourth surfaces 12, 13, and a front and a rear surfaces 14, 15 with no seam on the first surface 10, and open at the other end 48 (e.g., a gusseted bag structure). Each side gusset 12b, 13b is located at the respective third or fourth surface 12, 13. Referring to FIG. 1C, the package has a length PH, a width PW and a height PH.

In some embodiments, each of the third and fourth surfaces 12, 13 of the package 1 comprises a fourfold portion in the side gusset 12b, 13b where the side seam 12a, 13a is formed. The fourfold portion in the side seam 12a, 13a has two inner layers and two outer layers, and each of the two inner layers comprises an area consisting of the film layer. In one of the embodiments, each of the two inner layers consists of the film layer. In the embodiments, the first surface may comprise an area consisting of a film layer. In one of the embodiments, the first surface may consist of a film layer.

In another embodiment, each of the third and fourth surfaces 12, 13 of the package 1 consists of a twofold portion. In the embodiment, each of the first and second side seams is a twofold portion consisting of two laminate layers.

Still referring to FIGS. 1B and 1C, the second surface 11 of the package 1 comprises a fourfold portion in a closing gusset 11b along the closing seam 11a, and a twofold portion along the closing seam 11a. the second surface comprising an area consisting of the film layer where the closing seam 11a is formed.

The bag 4 may be filled by inserting articles such as a stack of absorbent articles through the open end 48. As may be appreciated from FIGS. 1B and 1C, the open end 48 opposite first surface 10 may then be closed by suitably folding to form closing gussets 11b, bringing the partial laminate edges together, and bonding them together to form an closing seam 11a and an closing seam fin 11c extending from the closing seam 11a, and second surface 11. When the bag 4 is filled with a plurality of articles, e.g. by entering articles from the open end 48, the appropriate device used to introduced the articles inside the bag 4 together with the articles may exert some tension on each of the third and fourth surfaces 12, 13 of the bag 4. The articles when they were compressed before being inserted in to the bag 4 may slightly expand after they are introduced in the bag 4 and thus exert some tension at the third and fourth surfaces 12, 13. The tension are exerted on each of the gusset 12b, 13b at the respective third and fourth surfaces 12, 13, particularly along the first and second side seams 12a, 13a with which the package may maintain a substantially parallelepiped-shape.

The bag 4 and package 1 dimensions may be suitably selected and effected through design, folding, stacking, compression and packaging processes so that the package 1 retains the product and maintains a neat, stable, a substantially parallelepiped-shape, i.e. a cuboid shape of the package 1.

In one embodiment, the first surface 10 may be a top surface of the package 1 as shown in FIG. 1C. In another embodiment, the first surface 10 may be a bottom surface of the package 1.

The package of the present invention comprises a laminate comprising a film layer and a paper layer. The laminate may comprises a pattern. A "pattern" herein is used to describe the individual's perception of spatial variation of visible light due to contrasts in spatial variation of light due to the color, form, texture, or any combination thereof. The pattern may be formed by printing, embossing, or a laminate production method. In one embodiment, a paper layer comprises a pattern, In another embodiment, the film layer comprises a pattern.

The package of the present invention may include a carrying handle. In one example a carrying handle may be formed of a strip of film. The strip may be bonded by any suitable mechanism to portions of the package. In another example, a carrying handle may be formed of an extension of a closing seam fin 11c extending from a closing seam 11a, referring to FIG. 1B.

The package may comprise a plurality of compressed articles, e.g. compressed disposable absorbent articles. For example, the package 1 of the present invention may be used for accommodating a plurality of sanitary napkins or diapers. The absorbent articles may be folded and the plurality of folded articles may be arranged in one or more rows within the package. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 2:
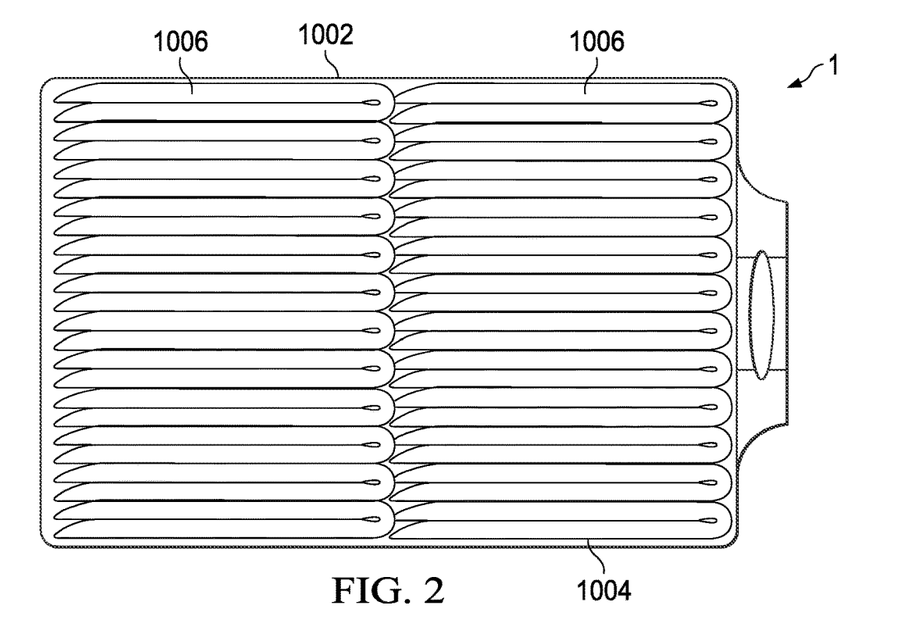
FIG. 2 is a side view of a package of the present invention containing a plurality of absorbent articles.

FIG. 2 illustrates an example package 1 comprising a plurality of absorbent articles 1004. Gussets are not indicated in FIG. 2. The package 1 defines an interior space 1002 in which the plurality of absorbent articles 1004 are situated. The plurality of absorbent articles 1004 are arranged in one or more stacks 1006.

Laminate

A package according to the present invention, and a package blank and a wicket bag suitable for forming thee package comprise a laminate comprising a film layer and a paper layer. The laminate is flexible such that the package may assume the parallelepiped-shape when it is filled with articles. The laminate further comprises an area consisting of the film layer.

In one embodiment, the package of the present invention, or the blank or the wicket bag suitable for forming the package comprises a laminate comprising a first paper layer, a second paper layer and a film layer sandwiched between the first and second paper layers.

Film Layer

The film layer in the laminate may be a single layer (monolayer), or may have two, three or more layers (multilayer). A multilayer film may have, for example, a first skin layer formed of a first polymer and a second skin layer formed of a second polymer.

In an application such as described herein, a multilayer film may be preferred. A multilayer film may have layers of polymer compositions particularly chosen for the characteristics they impart to the film. For example, one or two skin layers may be formed of compositions chosen for, e.g., surface gloss; printability; smooth feel; pliability; low noise generation (upon being handled and manipulated, as by a consumer); relatively lower melt temperature and fusibility/weldability; or any combination of these characteristics. One or more intermediate layers may be formed of compositions chosen for, e.g., tensile strength; stiffness; toughness; suitability for inclusion of blended-in recycled material; environmentally-friendly and/or sustainable material sourceability; relatively higher melt temperature; co-extrusion compatibility with adjacent layers (such that strong bonding between layers occurs upon co-extrusion); or any combination of these characteristics. It will be appreciated that a package having the configuration depicted in FIGS. 1B and 1C requires the film to be welded to itself on both sides—on the generally outer film surface at the gussets 11b, 12b and 13b, and on the generally inner film surface along all other portions of the seams 11a, 12a and 13a.

A multilayer film may include first outside skin layer, second outside skin layer, and/or intermediate layer disposed between the skin layers.

Each of the layers may include a base polymer. Base polymers may include polyolefins, particularly polyethylenes, polypropylenes, polybutadienes, polypropylene-ethylene interpolymer and copolymers having at least one olefinic constituent, and any mixtures thereof.

For purposes of balancing economy of polymer usage and maximization of tensile strength of the film, it may be desired that the total caliper of the film fall within a range of from 40 μm to 100 μm, more preferably from 50 μm to 90 μm, and even more preferably from 60 μm to 80 μm.

A film layer in the laminate may comprise small amounts of one or more additives. Some non-limiting examples of classes of additives contemplated include perfumes, dyes, pigments, nanoparticles, antistatic agents, fillers, and combinations thereof.

Paper Layer

"Paper", used herein related to a paper layer, intends to include synthetic paper as well as natural paper. Natural paper may manufactured from a composition comprising natural fibers such as cotton, silk, wool, hemp, pulp, and the like; or reclaimed fibers such as rayon, cupra. For example, the paper layer comprises cellulose-based fibers. The term "cellulose-based fibers", as used herein, intends to include both cellulose fibers such as pulp and cotton, and regenerated cellulose fiber such as rayon unless specified differently. Synthetic paper may be manufactured from a composition comprising plastic fibers such as polyethylene and polypropylene and the like. Examples of natural paper includes COLOR SILK PAPER from Mi Sung Paper CO. (Korea).

A basis weight of the paper layer may be in the range of from about 10 gsm to about 200 gsm. Paper type and an appropriate basis weight may be selected depending on package application areas, processibility in lamination, wicket bag folding, and/or package folding process.

The laminate comprising a film layer and a paper layer may be produced by combining the film layer and the paper layer together using adhesive. Suitable adhesive includes, but are not limited to, solvent-based adhesive, acrylic water-based adhesive, and solvent-less adhesive. The combined film and paper layers may be thermally and/or chemically cured. At least one of the film and paper layer may be printed before combined together. In one embodiment, the lamination is conducted continuously in a web width similar to a width of previous transformations in film making and/or optional printing. The laminate may be produced according to a conventional extrusion bonded laminate production process by extruding a molten film directly on to a paper layer.

Package Blank

The present invention also provides a package blank suitable for manufacturing a flexible gusset package in a substantially parallelepiped-shape containing a plurality of items wherein the package comprises a laminate comprising a film layer and a paper layer, the film layer facing the interior compartment.

By a "gusset" it is meant a member, for example a triangular member, capable of strengthening and/or enlarging the flexible package. The gusset when it is an extension of the laminate from which the flexible package is constructed, is formed folding the laminate from which the package is constructed, and has a fourfold portion. When the fourfold portion need to be heat-sealed, it may leave the fourfold portion unsealed due to the paper layer which is not heat-sealable when conventional automated gusseted polymeric film bag making and packing process. The package blank according to the present invention enable to use a natural or nature-looking material which is not heat-sealable while maintaining manufacturing feasibility of automated gusseted polymeric film bag making and packing operations.

Figure 3:
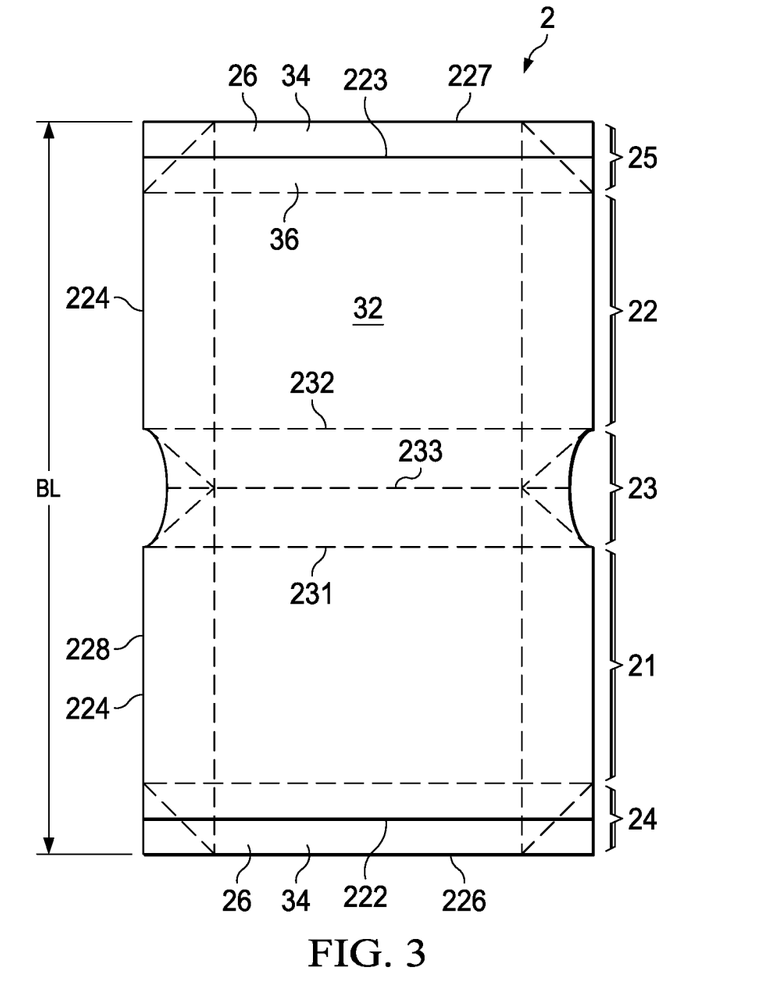
FIG. 3 is a front view of an exemplary package blank of the present invention.
Figure 4:
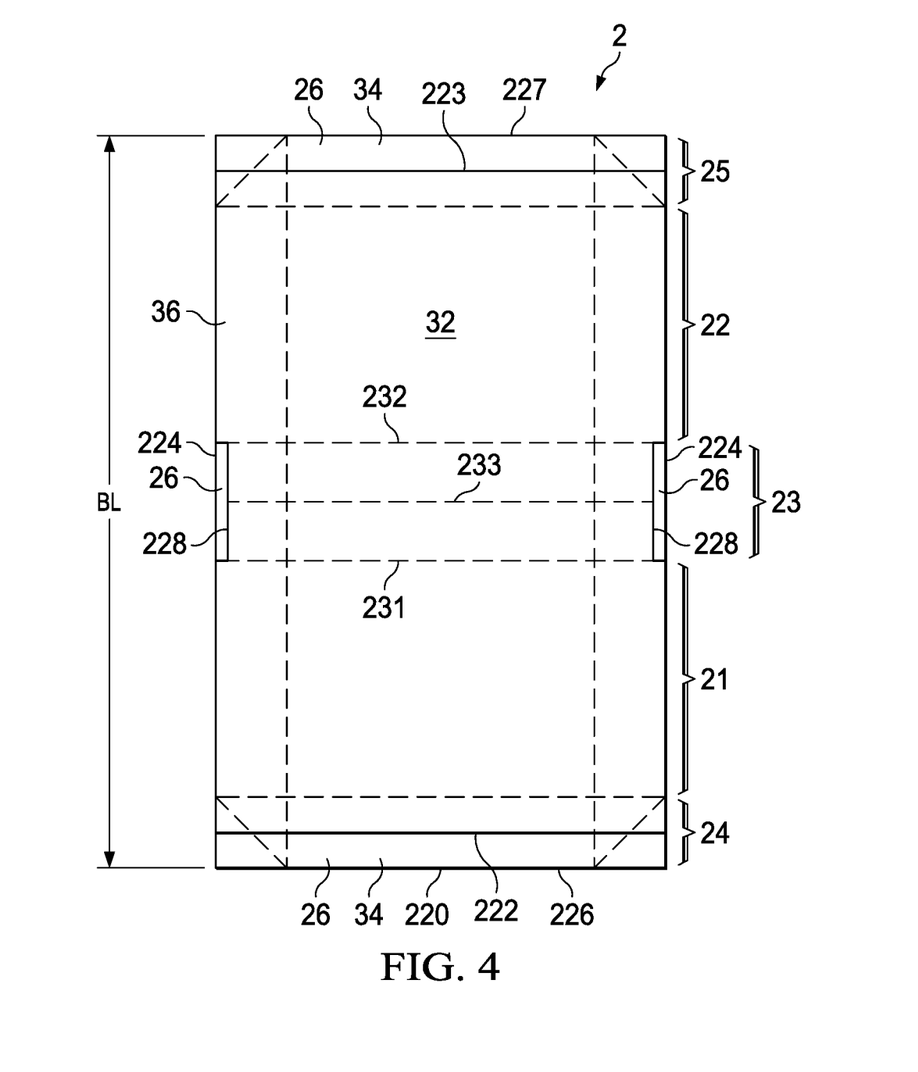
FIG. 4 is a front view of another exemplary package blank of the present invention.
Figure 5:
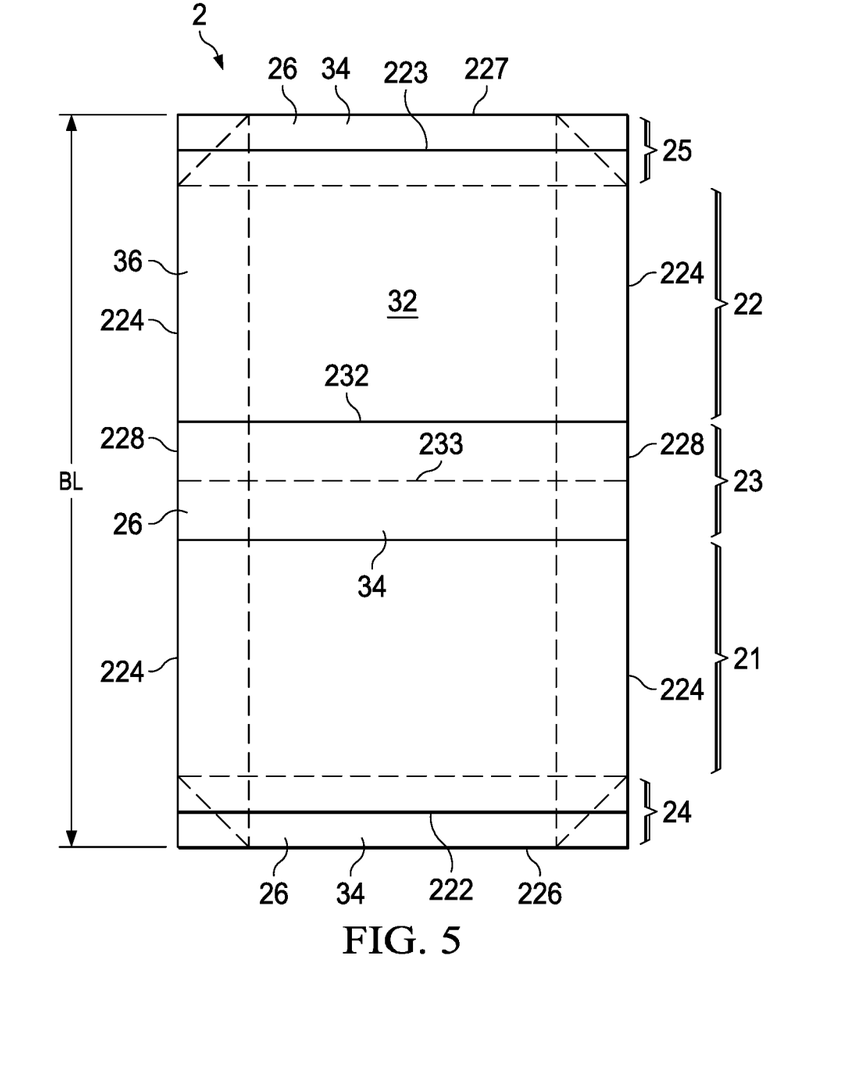
FIG. 5 is a front view of another exemplary package blank of the present invention.

FIGS. 3-5 show top views of exemplary blanks 2, before any folding has been performed to manufacture and form the package 1 from the laminate 32 comprising a film layer 34 and a paper layer 36. The blank 2 has a blank length BL, and comprises blank lateral edges 224 along the blank length BL, a first blank longitudinal edge 226, a second blank longitudinal edge 227, a first panel 21, a second panel 22, a third panel 23 located between the first and second panels 21, 22, a fourth panel 24 adjacent the first panel 21 opposite the third panel 23, and fifth panel 25 adjacent the second panel 22 opposite the third panel 23.

Referring to FIGS. 1B, 1C and 3-5, the first panel 21 forms the front surface 14 and a portion of each of the third and fourth surfaces 12, 13 of the package 1. A second panel 22 forms the rear surface 15 and a portion of each of the third and fourth surfaces 12 and 13 of the package 1. The first and the second panels 21, 22 are connected to each other at the third and fourth surfaces all 12, 13 along first and second side seams 12a, 13a. The first and second side seams 12a, 13a extend from the first surface 10 of the package 1 to the second surface 11 of the package 1. In one embodiment, the first panel 21 and the second panel 22 have a substantially the same length.

Referring to FIGS. 1B, 1C and 3-5, third panel 23 located between the first and second panels 21, 22 forms the first surface 10 and a pair of side gussets 12b, 13b of the package 1. The first and second internal surfaces 16 and 17 of each gusset 12b, 13b are made of triangular portions of the third panel 23. When making the package 1 from a laminate 32, the laminate 32 in the form of an endless sheet is folded over itself multiple times so as to form a generally M-shaped film. The laminate 32 is folded along a first, second and medial fold lines 231, 232, 233, as shown for instance in FIGS. 3-5. The first, second and medial fold lines 231, 232, 233 extend in a machine direction. A third panel 23 is delimited by the two outer fold lines 231, 232.

Still referring to FIGS. 1B, 1C and 3-5, the fourth panel 24 forms a portion of the second surface 11 and a portion of a pair of closing gussets 11b of the package 1. A fifth panel 25 forms a portion the second surface 11 of the package 1 and a portion of a pair of closing gussets 11b. The fourth and fifth panels 24, 25 are connected to each other at the second surface 11 along the closing seam 11a. Referring FIGS. 3-5, each of the fourth and fifth panels 24, 25 comprises an area 26 essentially consisting of the film layer where the closing seam is formed when the package blank is converted into the package. The area 26 in the fourth panel 24 is surrounded by a first laminate longitudinal edge 222, blank lateral edges 224, and a first blank longitudinal edge 226. The area 26 in the fifth panel 25 is surrounded by a second laminate longitudinal edge 223, blank lateral edges 224, and a second blank longitudinal edge 227. In one embodiment, each of the fourth and fifth panels 24, 25 consists of the film layer. In another embodiment, either one of the fourth panel 4 and the fifth panel 25 has a length longer than the other.

Referring to FIG. 3, in some embodiments, the blank 2 comprises a third panel 23 comprising opposing recessed blank lateral edges 224. When the blank 2 is converted into a package 1, referring to FIGS. 1B, 1C and 4, the package 1 comprises a side gusset 12b, 13b having a twofold portion in an area where a side seam 12a, 13a is formed.

Referring to FIGS. 4 and 5, in some embodiments, a blank 2 comprises a third panel 23 comprising an area 26 adjacent each of a blank lateral edges 224, the area 26 consisting of a film layer. In one of the embodiments, referring to FIG. 4, the area 26 in the third panel 23 may be surrounded by the blank lateral edge 224, a film lateral edge 228, and a first and second fold lines 231, 232 in the third panel 23. In another embodiment, referring to FIG. 5, the third panel 23 consists of a film layer. In the embodiments, when the blank 2 is converted into a package 1, referring to FIGS. 1B and 1C, the package 1 comprises a side gusset 12b, 13b having a fourfold portion in an area where a side seam 12a, 13a is formed. The fourfold portion in the side seam 12a, 13a has two inner layers from the third panel 23 and two outer layers each of which is from the first panel 21 and second panel 22, respectively.

Wicket Bag

The present invention provides a wicket bag suitable for producing the package according to the present invention. The wicket bag has a substantially folded flat-shape able to be converted into an unfolded package configuration having a substantially cuboid shape. The wicket bag comprises a laminate comprising a film layer and a paper layer.

Figure 6A:
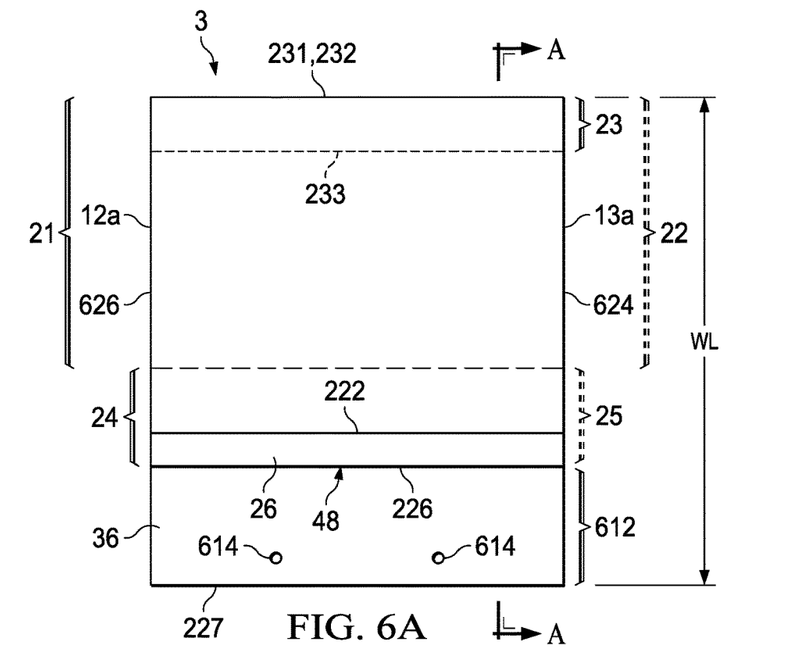
FIG. 6A is a front view of an exemplary folded wicket bag of the present invention.
Figure 6B:
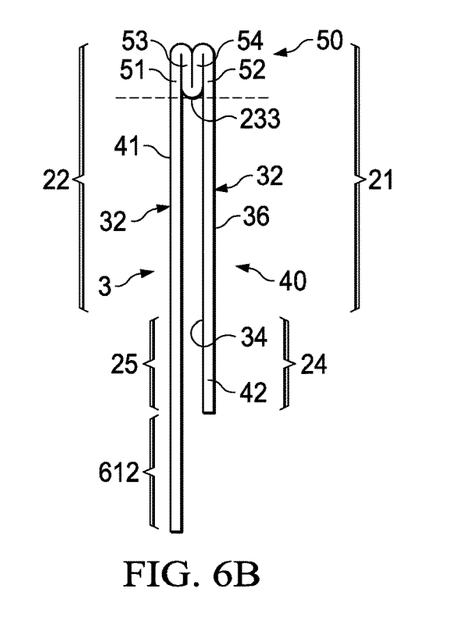
FIG. 6B is a cross-sectional view of the wicket bag of FIG. 6A along a line A-A.

As shown in FIGS. 6A and 6B, prior to inserting articles into a bag and being converted into a package of the present invention, the bag may be configured as a wicket bag 3. The wicked bag 3 has a wicked bag length WL, and a first and second wicked lateral edges 621, 624 along the wicked bag length direction. A first side seam 12a and a second side seam 13a are formed along the wicked lateral edges. The wicket bag 3 comprises a first panel 21 having a first lateral edge and a second lateral edge; a second panel 22 opposite the first panel 21, the second panel having a first lateral edge and a second lateral edge, wherein the first panel 21 and second panel 22 are connected to each other along the first and second lateral edges; a third panel 23 located between the first and second panels 21, 22, the third panel 23 having a first lateral edge and a second lateral edge; a fourth panel 24 adjacent the first panel 21 opposite the third panel 23; a fifth panel 25 adjacent the second panel 22 opposite the third panel 23; and a wicket panel 612 adjacent the fifth panel 25 opposite the third panel 23. In the wicket bag 3, each of the fourth and fifth panels 24, 25 comprises an area 26 essentially consisting of the film layer where a closing seam is formed when the wicket bag 3 is converted into a package for example shown in FIG. 1C. In one embodiment, each of the fourth and fifth panels 24, 25 consists of the film layer.

The first side seam 12a joins the first lateral edges of the first and fourth panels 21, 24 and the first lateral edges of the second and fifth panels 22, 25. The second side seam 13a joins the second lateral edges of the first and fourth panels 21, 24 and the second lateral edges of the second and fifth panels 22, 25.

Still referring to FIGS. 6A and 6B, the wicket bag 3 of the present invention comprises a twofold portion 40 and a fourfold portion 50 extended along the wicket length direction. The twofold portion 40 comprises a first and a second layers 41, 42, and the fourfold portion 50 comprises a first and a second outer layers 51, 52 and a first and a second inner layers 53, 54. The first and second outer layers 51, 52 of the fourfold portion 50 which are parts of the first panel 21 and the second panel 22, respectively are coextensive with the first and second layers 41, 42 of the twofold portion 40, so that the first layer 41 of the twofold portion 40 and the first outer layer 51 of the fourfold portion 50 form the first panel 21, and the second layer 42 of the twofold portion 40 and the second outer layer 52 of the fourfold portion 50 form the second panel 22. The third panel 23 forms the first and second inner layers 53, 54 of the fourfold portion 50 which mutually merge at the medial fold line 233. Each inner layer 53, 54 merges into the respective adjacent outer layer 51, 52 at the respective first and second fold lines.

The wicket panel 612 comprises at least one wicket aperture 174, each wicket aperture 614 configured to receive a wicket. As shown in FIG. 6A, the wicket panel 612 may include two wicket apertures 174. The wicket panel 612 may extend beyond the bottom edge 226 of the fifth panel 25 such that the wicket panel 612 does not overlap the fifth panel 25.

In some embodiments, the third panel 23 has an area adjacent each of the first and second lateral edges consisting of the film layer where each of the first and second side seams 12a, 13a is formed, respectively. A wicket bag configuration of the embodiments enables to produce a wicket bag with a laminate comprising a film layer and a paper layer using an automated process for producing gusseted thermoplastic film bags and a packing process using the same. In one of the embodiments, at least part of the area adjacent the lateral edge consists of the film layer. In one of the embodiments, the area adjacent the later edge along the entire lateral edge of the third panel 23 consists of the film layer.

In other embodiments, the first and second lateral edges of the third panel are recessed between first and second side seams. In other words, in the fourfold portion 50, the first and second inner layers have first and second lateral edges recessed than the first and lateral edges of the first and second outer layers. The wicket bag of this configuration also enables to produce a wicket bag with a laminate comprising a film layer and a paper layer using an automated producing process for gusseted thermoplastic film bag.

Referring to FIGS. 1B and 6A, in the wicket bag 3, the first panel 21 forms the front surface 14 and a portion of each of the third and fourth surfaces 12, 13 of the package 1; the second panel 22 forms the rear surface 15 and a portion of each of the third and fourth surfaces 12 and 13 of the package 1; a third panel 23 located between the first and second panels 21, 22, forms the first surface 10 and a pair of side gussets 12b, 13b of the package 1; a fourth panel 24 forms a portion of the second surface 11 and a pair of closing gussets 11b of the package 1; and a fifth panel 25 forms a portion the second surface 11 of the package 1 and a pair of closing gussets 11b. The fourth and fifth panels 24, 25 are connected to each other at the second surface 11 along the closing seam 11a. each of the fourth and fifth panels 24, 25 comprises an area 26 essentially consisting of the film layer where the closing seam is formed when the package blank is converted into the package.

The wicket bag 3 may be filled with articles such as absorbent articles by inserting the articles through the open end 48. Once the wicket bag 3 is open to form an open bag similar to one shown in FIG. 1A and filled with articles, the open end 48 may then be closed by suitably folding the fourth and fifth panels 24, 25 to form closing gussets 11b and a closing seam 11a as stated with respect to bag 4 above. Additionally, the wicket panel 612 may be cut away from the fifth panel 25 to form the package 1 such as shown in FIGS. 1B and 1C. In some exemplary configurations, the steps of forming the closing seam 11a and cutting the wicket panel 612 may occur concurrently. In other exemplary configurations, the steps of forming the closing seam 11a and cutting the wicket panel 612 may occur sequentially.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 2). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package accommodating a plurality of items, the package having a length, a width and a height, and the package comprising
    a front surface;
    a rear surface opposite the front surface;
    a first surface adjacent the front and rear surfaces, the first surface having no seam thereacross;
    a second surface opposite the first surface, the second surface having a closing seam extending along a direction of the package width;
    an opposing pair of third and fourth surfaces respectively adjacent the first and second surfaces, the third and fourth surfaces having a first side seam and a second side seam, respectively, extending therealong along a direction of the package height;
    a pair of side gussets each of which is located at the third and fourth surfaces, respectively; and
    a pair of closing gussets located in the second surface,
    wherein the surfaces cooperatively define an interior compartment of the package,
    wherein the package comprises a laminate comprising a film layer and a paper layer, the film layer facing the interior compartment, and
    wherein the second surface comprises an area essentially consisting of the film layer where the closing seam is formed.

2. The package according to claim 1, wherein the package comprises a laminate comprising a first paper layer, a second paper layer and a film layer sandwiched between the first and second paper layers.

3. The package according to claim 1, wherein the second surface comprises a fourfold portion.

4. The package according to claim 1, wherein each of the first and second side seams comprises a fourfold portion in the first and second side gussets, respectively, the fourfold portion having two inner layers and two outer layers, wherein each of the two inner layers comprising an area consisting of the film layer.

5. The package according to claim 4, wherein each of the first surface comprises an area consisting of the film layer.

6. The package according to claim 1, wherein each of the first and the second side seams consists of a twofold portion.

7. The package according to claim 1, wherein the laminate comprises a pattern.

8. The package according to claim 7, wherein the paper layer comprises a pattern.

9. The package according to claim 1, wherein the paper layer comprises natural paper.

10. The package according to claim 1, wherein the items are absorbent articles.

11. The package according to claim 1, wherein the package comprises absorbent articles and has an In-Bag Stack Height of less than about 110 mm.

12. The package according to claim 11, wherein the absorbent articles are diapers, adult incontinence briefs, or training pants.

13. A package blank formable into a package for accommodating a plurality of items, the package blank having a pair of lateral edges,
    wherein the package comprises
    a front surface;
    a rear surface opposite the front surface;
    a first surface adjacent the front and rear surfaces, the first surface having no seam thereacross;
    a second surface opposite the first surface, the second surface having a closing seam extending along a direction of the package width;
    an opposing pair of third and fourth surfaces respectively adjacent the first and second surfaces, the third and fourth surfaces having a first side seam and a second side seam, respectively, extending therealong along a direction of the package height;

a pair of side gussets each of which is located at the third and fourth surfaces, respectively; and a pair of closing gussets located in the second surface, wherein the surfaces cooperatively define an interior compartment of the package, wherein the package blank comprises a first panel forming the front surface and a portion of each of the third and fourth surfaces;

a second panel forming the rear surface and a portion of each of the third and fourth surfaces;

a third panel located between the first and second panels, the third panel forming the first surface and the pair of the side gussets, wherein the third panel comprises two opposing lateral edges;

a fourth panel adjacent the first panel opposite the third panel, the fourth panel forming a portion of the second surface and a portion pair of closing gussets; and a fifth panel adjacent the second panel opposite the third panel, the fifth panel forming a portion of the second surface and a portion pair of closing gussets, wherein the package blank comprises a laminate comprising a film layer and a paper layer, wherein the third panel comprises an area adjacent each of the lateral edges, the area essentially consisting of the film layer, and wherein each of the fourth and fifth panels comprises an area essentially consisting of the film layer where the closing seam is formed when the package blank is converted into the package.

14. The package blank according to claim 13, wherein the package blank comprises a laminate comprising a first paper layer, a second paper layer and a film layer sandwiched between the first and second paper layers.

15. The package blank according to claim 13, wherein the third panel essentially consists of the film layer.

16. A package blank formable into a package for accommodating a plurality of items, the package blank having a pair of lateral edges, wherein the package comprises a front surface;

a rear surface opposite the front surface;

a first surface adjacent the front and rear surfaces, the first surface having no seam thereacross;

a second surface opposite the first surface, the second surface having a closing seam extending along the direction of the package width;

an opposing pair of third and fourth surfaces respectively adjacent the first and second surfaces, the third and fourth surfaces having a first side seam and a second side seam, respectively, extending therealong along a direction of the package height;

a pair of side gussets each of which is located at the third and fourth surfaces, respectively; and a pair of closing gussets located in the second surface, wherein the surfaces cooperatively define an interior compartment of the package, wherein the package blank comprises a first panel forming the front surface and a portion of each of the third and fourth surfaces;

a second panel forming the rear surface and a portion of each of the third and fourth surfaces;

a third panel located between the first and second panels, the third panel forming the first surface and the pair of the side gussets, wherein the third panel comprises recessed lateral edges;

a fourth panel adjacent the first panel opposite the third panel, the fourth panel forming a portion of the second surface and a portion of a pair of the closing gussets; and a fifth panel adjacent the second panel opposite the third panel, the fifth panel forming a portion of the second surface and a portion pair of closing gussets, wherein the package blank comprises a laminate comprising a film layer and a paper layer, and wherein each of the fourth and fifth panels comprises an area essentially consisting of the film layer where the closing seam is formed when the package blank is converted into the package.

17. The package blank according to claim 16, wherein the package blank comprises a laminate comprising a first paper layer, a second paper layer and a film layer sandwiched between the first and second paper layers.

* * * * *